US006489101B1

(12) United States Patent
Dillon

(10) Patent No.: US 6,489,101 B1
(45) Date of Patent: Dec. 3, 2002

(54) COMPOSITIONS AND METHODS FOR THERAPY AND DIAGNOSIS OF BREAST CANCER

(75) Inventor: Davin C. Dillon, Issaquah, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/451,651

(22) Filed: Nov. 30, 1999

(51) Int. Cl.$^7$ .......................... C12Q 1/68; C12P 19/34; A01N 43/04; A61K 38/00; C07H 21/02

(52) U.S. Cl. .......................... 435/6; 435/91.2; 530/300; 514/44; 536/23.1

(58) Field of Search ................... 435/6, 91.2; 536/23.1; 514/44; 530/300

(56) References Cited

U.S. PATENT DOCUMENTS 5,654,172 A    8/1997   Li et al. .................... 435/69.1

FOREIGN PATENT DOCUMENTS

| WO | WO 96/06862 | 3/1996 |
| WO | WO 97/25431 | 7/1997 |
| WO | WO 99/14230 | 3/1999 |
| WO | WO 99/37775 | 7/1999 |
| WO | WO 99/33869 | 9/1999 |

OTHER PUBLICATIONS

Sequence Homology Search.*
Struck, M., "Vaccine R&D success rates and development times," Nature Biotechnology, 1996, vol. 14, pp. 591–593.*
Taubes, G., "Salvation in a Snippet of DNA?," Science, 1997, vol. 278, pp. 1711–1714.*
Watson et al., "Isolation of Cloned Genes," Chapter 6, Recombinant DNA, 1983, pp. 72–90.*
Burger et al., "Breast Cancer Genome Anatomy: Correlation of Morphological Changes in Breast Carcinomas with Expression of the Novel Gene Product Di12," *Oncogene* 16:327–333, 1998.
Diatchenko et al., "Suppression subtractive Hybridization: A Method for Generating Differentially Regulated or Tissue–Specific cDNA Probes and Libraries," *PNAS* 93:6025–6030, Jun. 1996.
Lee et al., "Positive Selection of Candidate Tumor–Suppressor Genes by Subtractive Hybridization," *PNAS* 88:2825–2829, Apr. 1991.
Schlom et al., "Strategies for the development of recombinant vaccines for the immunotherapy of breast cancer," *Breast Cancer Research and Treatment* 38(1):27–39, 1996.
Hara et al., "Characterization of cell phenotype by a novel cDNA library subtraction system: expression of CD8α in a mast cell–derived interleukin–4–dependent cell line," *Blood* 84(1):189–199, Jul. 1, 1994.
Hedblom and Kirkness, "A novel class of GABA$_A$ receptor subunit in tissues of the reproductive system," *The Journal of Biological Chemistry* 272(24):15346–15350, Jun. 13, 1997.
Porter–Jordan and Lippman, "Overview of the biologic markers of breast cancer," *Breast Cancer* 8(1):73–100, Feb. 1994.

* cited by examiner

Primary Examiner—John S. Brusca
Assistant Examiner—Young Kim
(74) Attorney, Agent, or Firm—Seed Intellectual Property Law Group PLLC

(57) ABSTRACT

Compositions and methods for the therapy and diagnosis of cancer, such as breast cancer, are disclosed. Compositions may comprise one or more breast tumor proteins, immunogenic portions thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

2 Claims, No Drawings

COMPOSITIONS AND METHODS FOR THERAPY AND DIAGNOSIS OF BREAST CANCER

TECHNICAL FIELD

The present invention relates generally to therapy and diagnosis of cancer, such as breast cancer. The invention is more specifically related to polypeptides comprising at least a portion of a breast tumor protein, and to polynucleotides encoding such polypeptides. Such polypeptides and polynucleotides may be used in vaccines and pharmaceutical compositions for prevention and treatment of breast cancer, and for the diagnosis and monitoring of such cancers.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, Breast Cancer 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the present invention provides compositions and methods for the diagnosis and therapy of cancer, such as breast cancer. In one aspect, the present invention provides polypeptides comprising at least a portion of a breast tumor protein, or a variant thereof Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in SEQ ID NO: 1–35; (b) variants of a sequence recited in SEQ ID NO: 1–35; and (c) complements of a sequence of (a) or (b).

The present invention further provides polynucleotides that encode a polypeptide as described above, or a portion thereof (such as a portion encoding at least 15 amino acid residues of a breast tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a breast tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be breast cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a breast tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

SEQUENCE IDENTIFIERS

SEQ ID NO: 1 is the determined cDNA sequence for clone 26915.

SEQ ID NO: 2 is the determined cDNA sequence for clone 26914.

SEQ ID NO: 3 is the determined cDNA sequence for clone 26673.

SEQ ID NO: 4 is the determined cDNA sequence for clone 26672.

SEQ ID NO: 5 is the determined cDNA sequence for clone 26671.

SEQ ID NO: 6 is the determined cDNA sequence for clone 26670.

SEQ ID NO: 7 is the determined cDNA sequence for clone 26669.

SEQ ID NO: 8 is a first determined cDNA sequence for clone 26668.

SEQ ID NO: 9 is a second determined cDNA sequence for clone 26668.

SEQ ID NO: 10 is the determined cDNA sequence for clone 26667.

SEQ ID NO: 11 is the determined cDNA sequence for clone 26666.

SEQ ID NO: 12 is the determined cDNA sequence for clone 26665.

SEQ ID NO: 13 is the determined cDNA sequence for clone 26664.

SEQ ID NO: 14 is the determined cDNA sequence for clone 26662.

SEQ ID NO: 15 is the determined cDNA sequence for clone 26661.

SEQ ID NO: 16 is the determined cDNA sequence for clone 26660.

SEQ ID NO: 17 is the determined cDNA sequence for clone 26603.

SEQ ID NO: 18 is the determined cDNA sequence for clone 26601.

SEQ ID NO: 19 is the determined cDNA sequence for clone 26600.

SEQ ID NO: 20 is the determined cDNA sequence for clone 26587.

SEQ ID NO: 21 is the determined cDNA sequence for clone 26586.

SEQ ID NO: 22 is the determined cDNA sequence for clone 26584.

SEQ ID NO: 23 is the determined cDNA sequence for clone 26583.

SEQ ID NO: 24 is the determined cDNA sequence for clone 26580.

SEQ ID NO: 25 is the determined cDNA sequence for clone 26579.

SEQ ID NO: 26 is the determined cDNA sequence for clone 26577.

SEQ ID NO: 27 is the determined cDNA sequence for clone 26575.

SEQ ID NO: 28 is the determined cDNA sequence for clone 26574.

SEQ ID NO: 29 is the determined cDNA sequence for clone 26573.

SEQ ID NO: 30 is the determined cDNA sequence for clone 25612.

SEQ ID NO: 31 is the determined cDNA sequence for clone 22295.

SEQ ID NO: 32 is the determined cDNA sequence for clone 22301.

SEQ ID NO: 33 is the determined cDNA sequence for clone 22298.

SEQ ID NO: 34 is the determined cDNA sequence for clone 22297.

SEQ ID NO: 35 is the determined cDNA sequence for clone 22603.

DETAILED DESCRIPTION OF THE INVENTION

As noted above, the present invention is generally directed to compositions and methods for the therapy and diagnosis of cancer, such as breast cancer. The compositions described herein may include breast tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a breast tumor protein or a variant thereof A "breast tumor protein" is a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery human breast tumor proteins. Sequences of polynucleotides encoding specific tumor proteins are provided in SEQ ID NO: 1–35.

Breast Tumor Protein Polynucleotides

Any polynucleotide that encodes a breast tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a breast tumor protein. More preferably, a polynucleotide encodes an immunogenic portion of a breast tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native breast tumor protein or a portion thereof The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.O. (1978) A model of evolutionary change in proteins—Matrices for detecting distant relationships. In Dayhoff, M.O. (ed.) Atlas of Protein Sequence and Structure, National Biomedical Research Foundation, Washington DC Vol. 5, Suppl. 3, pp. 345–58; Hein J. (1990) Unified Approach to Alignment and Phylogenes pp. 626–645 *Methods in Enzymology vol.* 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof Such polynucleotide variants are capable of hybridizing under moderately stringent conditions to a naturally occurring DNA sequence encoding a native breast tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least two fold greater in a breast tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a breast tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Method Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Certain nucleic acid sequences of cDNA molecules encoding portions of breast tumor proteins are provided in SEQ ID NO: 1–35.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a breast tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a breast tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). ). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety,-such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Breast Tumor Polypeptides

Within the context of the present invention, polypeptides may comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may Generally be made on the basis of similarity in polarity, charge, solubility, hydrophobicity, hydrophilicity and/or the amphipathic nature of the residues. For example, negatively charged amino acids include aspartic acid and glutamic acid, positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85.2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NSI (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum urine and/or tumor biopsies ) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. Irvine, Calif. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a breast tumor polypeptide (100 ng/ml–100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley lnterscience (Greene 1998)). T cells that have been activated in response to a breast tumor polypeptide, polynucleotide or polypeptide-expressing APC may be $CD4^+$ and/or $CD8^-$. breast tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Compositions And Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e:g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad Sci. USA* 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Nati. Acad Sci. USA* 90:11498–11502, 1993; Guzman et al., *Circulation* 88:2838–2848, 1993; and Guznan et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, Bortadellapertussis or Mycobacterium tuberculosis derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1-type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med 50:507–529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the breast tumor polypeptide, DNA (naked or within a plasmid vector) or RNA, or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as breast cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays, which may be performed using samples obtained from a patient before and after treatment.

Methods For Detecting Cancer

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour arid about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group Qn the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level. of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising $CD4^+$ and/or $CD8^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 µg/ml). It may be desirable to incubate another aliquot of a T cell sample in the absence of breast tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–35. Techniques for both PCR based assays and hybridization assays are well known in the art (see, for example, Mullis et al., *Cold Spring Harbor Symp. Quant. Biol.*, 51:263, 1987, Erlich ed., PCR *Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the-disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLE 1

Identification of Breast Tumor Protein CDNAS

This Example illustrates the identification of cDNA molecules encoding breast tumor proteins.

A human metastatic breast tumor cDNA expression library was constructed from metastatic breast tumor poly A− RNA using a Superscript Plasmid System for cDNA Synthesis and Plasmid Cloning kit (BRL Life Technologies, Gaithersburg, Md. 20897) following the manufacturer's protocol. Specifically, breast tumor tissues were homogenized with polytron (Kinematica, Switzerland) and total RNA was extracted using Trizol reagent (BRL Life Technologies) as directed by the manufacturer. The poly A+ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BstX I adaptors (Invitrogen, Carlsbad, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen, Carlsbad, Calif.) and transformed into ElectroMax E. Coli DH10B cells (BRL Life Technologies) by electroporation.

Using the same procedure, a normal human breast cDNA expression library was prepared from a pool of four normal breast tissue specimens. The cDNA libraries were characterized by determining the number of independent colonies, the percentage of clones that carried insert, the average insert size and by sequence analysis. Sequencing analysis showed both libraries to contain good complex cDNA clones that were synthesized from mRNA, with minimal rRNA and mitochondrial DNA contamination sequencing.

A cDNA subtracted library (referred to as BS3) was prepared using the above metastatic breast tumor and normal breast cDNA libraries, as described by Hara et al. (*Blood*, 84:189–199, 1994) with some modifications. Specifically, a breast tumor-specific subtracted cDNA library was generated as follows. Normal breast cDNA library (70 µg) was digested with EcoRI, NotI, and SfuI, followed by a filling-in reaction with DNA polymerase Klenow fragment. After phenol-chloroform extraction and ethanol precipitation, the DNA was dissolved in 100 µl of $H_2O$, heat-denatured and mixed with 100 µl (100 µg) of Photoprobe biotin (Vector Laboratories, Burlingame, Calif.), the resulting mixture was irradiated with a 270 W sunlamp on ice for 20 minutes. Additional Photoprobe biotin (50 µl ) was added and the biotinylation reaction was repeated. After extraction with butanol five times, the DNA was ethanol-precipitated and dissolved in 23 µl $H_2O$ to form the driver DNA.

To form the tracer DNA, 10 µg breast tumor cDNA library was digested with BamFI and XhoI, phenol chloroform extracted and passed through Chroma spin-400 columns (Clontech). Following ethanol precipitation, the tracer DNA was dissolved in 5 µl $H_2O$. Tracer DNA was mixed with 15 µl driver DNA and 20 µl of 2× hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2× hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK+ (Stratagene, La Jolla, Calif. 92037) and transformed into ElectroMax E. coli DH10B cells by electroporation to generate a breast tumor specific subtracted cDNA library.

To analyze the subtracted cDNA library, plasmid DNA was prepared from independent clones, randomly picked from the subtracted breast tumor specific library and characterized by DNA sequencing with a Perkin Elmer/Applied Biosystems Division Automated Sequencer Model 373A (Foster City, Calif.).

A second cDNA subtraction library containing cDNA from breast tumor subtracted with normal breast cDNA, and known as BT, was constructed as follows. Total RNA was extracted from primary breast tumor tissues using Trizol reagent (Gibco BRL Life Technologies, Gaithersburg, Md.) as described by the manufacturer. The polyA+RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech. The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax E. coli DH10B cells (Gibco BRL Life, Technologies) by electroporation. DNA was isolated from independent clones and sequenced using a Perkin Elmer/Applied Biosystems Division (Foster City, Calif.) Automated Sequencer Model 373 A.

Two additional subtracted cDNA libraries were prepared from cDNA from breast tumors subtracted with a pool of cDNA from six normal tissues (liver, brain, stomach, small intestine, kidney and heart; referred to as 2BT and BC6) using the PCR-subtraction protocol of Clontech, described above.

cDNA clones isolated in the breast subtractions BS3, BT, 2BT and BC6, described above, were colony PCR amplified and their mRNA expression levels in breast tumor, normal breast and various other normal tissues were determined using microarray technology (Synteni, Fremont, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity.

The determined cDNA sequences of 35 clones determined to be over-expressed in breast tumor tissue compared to other tissues tested by a visual analysis of the microarray data are provided in SEQ ID NO: 1–35. Comparison of these cDNA sequences with known sequences in the gene bank using the EMBL and GenBank databases revealed no significant homologies to the sequences provided in SEQ ID NO: 7, 10, 21, 26 and 30. The sequences of SEQ ID NO: 2–5, 8, 9, 13, 15, 16, 22, 25, 27, 28, 33 and 35 showed some homology to previously isolated expressed sequences tags (ESTs), while the sequences of SEQ ID NO: 1, 6, 11, 12, 14, 17–20, 23, 24, 29, 31, 32 and 34 showed some homology to previously identified genes.

EXAMPLE 2

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A diagnostic kit, comprising:
   (a) an oligonucleotide probe that will hybridize under stringent conditions to SEQ ID NO:21; and
   (b) a diagnostic reagent for use in a hybridization assay.

2. A diagnostic kit, comprising:
   (a) two oligonucleotide primers, at least one of the oligonucleotide primers being specific for SEQ ID NO:21; and
   (b) a diagnostic reagent for use in a polymerase chain reaction assay.

* * * * *

SEQUENCE LISTING

<160> NUMBER OF SEQ ID NOS: 35

<210> SEQ ID NO 1
<211> LENGTH: 298
<212> TYPE: DNA
<213> ORGANISM: Homo sapiens

<400> SEQUENCE: 1

```
ctgaacagtg tcagctccgt gctggagaca gtcctgctga tcacctgaat gctgaacatg      60
cttcgtgggg ctatctttg tttctctgt agtctctttg gtgatctcat ctgcttttct      120
gctcgagtga tgacagcctt gaaccttgtc cttccttgtc tcagagggga aaaaggaatt      180
ggatttcctc agggtctggg gcctgggctg tggcttgagg ttccgagact gatgaatcca      240
agcatgcttg agggcctggt ccggggtcat gcgaagagaa ggttcccata ccaaacac       298
```

<210> SEQ ID NO 2
<211> LENGTH: 276
<212> TYPE: DNA
<213> ORGANISM: Homo sapiens

<400> SEQUENCE: 2

```
tggaaggtgt ggtgactaag ggccacggtt attgggtgaa atttgagatt gtaggccaac      60
tgtattttca agcttctgaa cttaggcaaa atattcatcg caaagtctct agcgtcatat      120
ttttctcacc taaattacgt ttccacgaga ttatttatat atagttggtc tatctctgca      180
gtccttgaag gtgaagttgt gtgttactag gctgtgtttt gggatgtcag cagtggcctg      240
aagtgagttg tgcaataaat gttaagttga aacctc                                 276
```

<210> SEQ ID NO 3
<211> LENGTH: 405
<212> TYPE: DNA
<213> ORGANISM: Homo sapiens -continued

```
<220> FEATURE:
<221> NAME/KEY: unsure
<222> LOCATION: (141)
<223> OTHER INFORMATION: n=A,T,C or G

<400> SEQUENCE: 3
tcacatggct atttcattta tttagtagtt ttgaaatgtt agcaaatata aggtatttgt      60
aaagcatctt tcattataaa gagattagta atattcacca atcatgccaa tgagattata    120
cactctgcca aagactacta naaaaatttg atcattatta aattcaatgt tatttgacag    180
tgtgaactct atgtaacagc acaaattctg gactttgaat ctggctgctg tcctcacctg    240
aaccattaaa atgaccttgt taacaaggaa ggaatcaatg gggaaatatc acaaccagag    300
attggctgtg tgtccaaggg tgctttgtct tgttgccagg atcagactgt gaaatcacag    360
aggcaagctg atgtcatcag aggtgactct gcccccaaca caatg                    405

<210> SEQ ID NO 4
<211> LENGTH: 696
<212> TYPE: DNA
<213> ORGANISM: Homo sapiens

<400> SEQUENCE: 4
cattgtgttg ggcactgtta cagtgaaacg gaaacgtgga aaatcacagc caaactgtgc     60
tctgaaagaa cactctatgt ctaatatagc cagcgtcaag agtccttatg aggcggagaa    120
ctccggggaa gagctggatc agaggtattc caaggccaag ccaatgtgta acacatgtgg    180
gaaagtgttt tcagaagcca gcagtttgag aaggcacatg agaatacata aaggagtcaa    240
accttacgtc tgccacttat gtggaaaggc atttacccaa tgtaaccagc tgaaaacgca    300
tgtaagaact catacaggtg agaagccata caaatgtgaa ttgtgtgata aggatttgc     360 tcagaaatgt cagctagtct tccatagtcg catgcatcat ggtgaagaaa aaccctataa    420
atgtgatgta tgcaacttac agtttgcaac ttctagcaat ctcaagattc atgcaaggaa    480
gcatagtgga gagaagccat atgtctgtga taggtgtgga cagagatttg ctcaagccag    540
cacactgacc tatcatgtcc gtaggcatac tggagaaaag ccttatgtat gtgatacctg    600
tgggaaggca tttgctgtct ctagttctct tatcactcat tctcgaaaac atacaggtaa    660
gtttgacagg gagagactgc ttaaaataaa gttata                              696

<210> SEQ ID NO 5
<211> LENGTH: 580
<212> TYPE: DNA
<213> ORGANISM: Homo sapiens
<220> FEATURE:
<221> NAME/KEY: unsure
<222> LOCATION: (332)
<223> OTHER INFORMATION: n=A,T,C or G

<400> SEQUENCE: 5
acatcaaaaa ggaaatattt ttgacttgct tttcttctgt aaatcctccc atctcactaa     60
tatttacaac aatccagagt agcgtttatg agacactgaa aaagacaggg aggaaatcct    120
ttttcaagat atgaagtcag aacctgaatg tagacatcgg acagagaagt cctcaaccac    180
aaacctgtcc tccagctcta gagagagtaa ggctgtatt ccaaccttga gatttttcat     240 tacatttttcc ccttttgggg tgttaaattc tttccaagaa tgctgtactt gtaaaaatga    300
ttttattcta gctacaaaac atttcattta anaaaaccgc atttttatatc cttgtgtgaa   360 atgctcccaa aagccatcaa gatatggaga caacagattt taaaaacata aatctaatca    420
```

-continued

| tatggcttg aaacagtatg aacatttaac agagtgacac gatatcatta ttatatttgt | 480 |
| ttgtcatgag atgaaaggcc tggaggcaga tggtgattaa tcataattcc tgagcttcta | 540 |
| cagaaatttt aaaatgaaat tactaactgc ttaaaattat | 580 |

<210> SEQ ID NO 6
<211> LENGTH: 557
<212> TYPE: DNA
<213> ORGANISM: Homo sapiens

<400> SEQUENCE: 6

| attacattca agataaaaga tttattcaca ccacaaaaag ataatcacaa caaaatatac | 60 |
| actaacttaa aaaacaaaag attatagtga cataaaatgt tatattctct ttttaagtgg | 120 |
| gtaaaagtat tttgtttgct tctacataaa tttctattca tgagagaata acaaatatta | 180 |
| aaatacagtg atagtttgca tttcttctat agaatgaaca tagacataac cctgaagctt | 240 |
| ttagtttaca gggagtttcc atgaagccac aaactaaact aattatcaaa cacattagtt | 300 |
| atttccagac tcaaatagat acacattcaa ccaataaact gagaaagaag catttcatgt | 360 |
| tctctttcat tttgctataa agcattttt cttttgacta aatgcaaagt gagaaattgt | 420 |
| attttttctc cttttaattg acctcagaag atgcactatc taattcatga gaatacgaa | 480 |
| atttcaggtg tttatcttct tccttacttt tggggtctac aaccagcata tcttcatggc | 540 |
| tgtgaaattc atggctg | 557 |

<210> SEQ ID NO 7
<211> LENGTH: 653
<212> TYPE: DNA
<213> ORGANISM: Homo sapiens

<400> SEQUENCE: 7

| cattgtgttg ggggaagtag ggaatattat tgaggcaggg taagaaatgg tttacaattc | 60 |
| tgaaaggatg atcaaagaaa aactcattgt tgagaaagta atatgagtag agacctgaaa | 120 |
| taagtgaggg agtgacgggt tatgtccagg gcaataatgt ttctgacaga ggggagagtc | 180 |
| atttcagaag cctagaggca tgtgtaaagc tgttagaatg ccagacagtc accaggccaa | 240 |
| gatgtgcaga tatccataag tgaagggaa agaaatacaa aatgaaggca gagaaatcac | 300 |
| aaaattggat aagtggtgcc ttgtaggcca tgatgatttt agttcatact aaaattgagt | 360 |
| taggctgcca ttgtagggtt tgtgagctca gggataacg ggtctgaatt ttatttctaa | 420 |
| aaggatcact ccaagtgtta cattgcaaag ataacgtaa ggtggctggt gtagtagact | 480 |
| aaagtggaat atagtaacag tgaaatacat tttgtggtaa agcttggtag atttgaccac | 540 |
| acaaaattgt gaattaccct gtggcacaaa aaatatcaaa ggtacataca gacagaagaa | 600 |
| ccttgcgatt gtttattaat gtccttaatt tataatgtta ataccagtag aag | 653 |

<210> SEQ ID NO 8
<211> LENGTH: 456
<212> TYPE: DNA
<213> ORGANISM: Homo sapiens

<400> SEQUENCE: 8

| cattgtgttg ggctaatcct tggtctctat ccaccctgcc tagcaattta tctcaaagct | 60 |
| tcaagttcct gccatctaca tgtgcccagg tcaaccaatc aatggctcag acagataagc | 120 |
| caacatgcat cccgccggag ctgccgaaaa tgctgaagga gtttgccaaa gccgccattc | 180 |
| gggcgcagcc gcaggacctc atccagtggg gggccgatta ttttgaggcc ctgtcccgtg | 240 |

```
gagagacgcc tccggtgaga gagcggtctg agcgagtcgc tttgtgtaac tgggcagagc      300
taacacctga gctgttaaag atcctgcatt ctcaggttgc tggcagactg atcatccgtg      360
cagaggagct ggcccagatg tggaaagtgg tgaatctccc aacagatctg tttaatagtg      420
tgatgaatgt gggtcgcttc acggaggaga tcgagt                                456
```

<210> SEQ ID NO 9
<211> LENGTH: 512
<212> TYPE: DNA
<213> ORGANISM: Homo sapiens

<400> SEQUENCE: 9

```
gtttttgatt cattttattt taacaatgtt taacaatgta agtccacata taagataccc       60
aagctttaaa tatctataca tataaactga tttcaacatc tttggcttca aaacagtaaa      120
attgtttttc caatatcaaa caagtcaaat ttggaaaagg cataaatctg tatgaacatc      180
ctgtatccat ggagatgtca tgactaaatt cagaaatagc ctcatctctc tttgtttttg      240
ctttcttatg tctgagttct gcatccaatt ctgtttatta catagttttc tataagattg      300 taccccttt  aaacagtgtc tattgatata tattctaggt gtctggaagt cttttttctat     360 agtcggctct tggttgtctc tgggaatatg aatggaagga gcagagtgaa aataaatctg      420
agggcaatat tcataaataa tccaagagct acactgtagt caactctccc cagagcctga      480
ccacagtgtt tccctctctc ctcctcccaa cc                                    512
```

<210> SEQ ID NO 10
<211> LENGTH: 308
<212> TYPE: DNA
<213> ORGANISM: Homo sapiens
<220> FEATURE:
<221> NAME/KEY: unsure
<222> LOCATION: (214)
<223> OTHER INFORMATION: n=A,T,C or G
<220> FEATURE:
<221> NAME/KEY: unsure
<222> LOCATION: (276)
<223> OTHER INFORMATION: n=A,T,C or G

<400> SEQUENCE: 10

```
atgtttatga agacctttaa atatttatat agaaacaaaa tgtcattgca acctaacatc       60
atccattaaa aataaaagga aaggaaaacg gcagggaaaa gtgcagtaat aacaaatggt      120
gacatgcttg gtcttaagca tcatagcaaa ctcattattt ccaatgaaac aaggattttt      180
agacccatct ttggaaatga ttcccaaatt aganaaccat caggtctcaa aaaaggaagg      240
gtcatcaaag tccatccagc ccagccaccc tgaggngcct gtatctcctc aacaagccca      300
acacaatg                                                              308
```

<210> SEQ ID NO 11
<211> LENGTH: 510
<212> TYPE: DNA
<213> ORGANISM: Homo sapiens
<220> FEATURE:
<221> NAME/KEY: unsure
<222> LOCATION: (98)
<223> OTHER INFORMATION: n=A,T,C or G
<220> FEATURE:
<221> NAME/KEY: unsure
<222> LOCATION: (327)
<223> OTHER INFORMATION: n=A,T,C or G

<400> SEQUENCE: 11

```
attatatgaa tattttaatg caaaatgctt aacacttaaa attagcaaag cgtcatttaa      60
attaaaattc catttaacta agatggtta accccaanaa attgtacagt agttgatttc     120
tgctatataa tgccagtcct atgccataca ataagaactg caacattagc tgtcacttcc    180
tccattgctc ttctggaccc taagggatga gggaggggac tcagacacaa aacacaaccc    240
aaataaactg tgcagtgatt cctaatagtt ataaacccaa tctaagttgt ccaaacagct    300
gaagaataac tgcaggtatt gttccanagc tgatacgagg ttttgctttt acagcctggt    360
aaaagttctg cactaggtga gaagtcacag tttaaggatg catgttctgt aaatagttac    420
tacatataca catttactgt ctgtaaacac tagaaatata cattagacag agtaccctca    480
caagttgggt acagtttaaa aaagaagatg                                     510

<210> SEQ ID NO 12
<211> LENGTH: 611
<212> TYPE: DNA
<213> ORGANISM: Homo sapiens
<220> FEATURE:
<221> NAME/KEY: unsure
<222> LOCATION: (196)
<223> OTHER INFORMATION: n=A,T,C or G

<400> SEQUENCE: 12
agttttataa aatattttat ttacagtaga gctttacaaa aatagtctta aattaataca     60
aatccctttt gcaatataac ttatatgact atcttctcaa aaacgtgaca ttcgattata    120
acacataaac tacattata gttgttaagt caccttgtat tataaatatg ttttcatctt    180
ttttttgtaa taaggnacat accaataaca atgaacaatg acaacaaat cttattttgt    240 tattcttcca atgtaaaatt catctctggc caaaacaaaa ttaaccaaag aaaagtaaaa    300
caattgtccc tctgttcaac aatacagtcc tttttaatta tttgagagtt tatctgacag    360
agacacagca ttaaactgaa agcaccatgg cataaagtct agtaacatta tcctcaaaag    420 cttttttccaa tgtctttcct tcaactgttt attcagtatt tggccagtac aaataaagat    480
tggtctcaac tctctctttc attagtctca agtgttccta ttatgcactg agttttcaga    540
ccttcccaac tggcatgtgt tttaagtgtg agtttctttc tttggcttca agtggagttt    600
cacaacattt a                                                          611

<210> SEQ ID NO 13
<211> LENGTH: 394
<212> TYPE: DNA
<213> ORGANISM: Homo sapiens
<220> FEATURE:
<221> NAME/KEY: unsure
<222> LOCATION: (62)
<223> OTHER INFORMATION: n=A,T,C or G
<220> FEATURE:
<221> NAME/KEY: unsure
<222> LOCATION: (91)
<223> OTHER INFORMATION: n=A,T,C or G
<220> FEATURE:
<221> NAME/KEY: unsure
<222> LOCATION: (105)
<223> OTHER INFORMATION: n=A,T,C or G
<220> FEATURE:
<221> NAME/KEY: unsure
<222> LOCATION: (195)
<223> OTHER INFORMATION: n=A,T,C or G
<220> FEATURE:
<221> NAME/KEY: unsure
<222> LOCATION: (294)
<223> OTHER INFORMATION: n=A,T,C or G

<400> SEQUENCE: 13
```

```
caatgtttag attcatttta ttagtggcat atacaaagca ccatataata tatgaaacgt    60
anaacaatca tgactatgta attaactgta naaataactg ctaanaaaat atagcaatat   120
ttaacacagg atttctaaaa ccattatatt ttcattactt ttcccaaagc taatgtccca   180
tgttttattt tatanacttt gtttatcaag atttatatgc atttggcacc tttttgggct   240
gaaaatagtt gatgtactct gtacagtaat gttacagttt tatacaaaat tcanaaatat   300
tgcatttgga atagtcttta tggtcctctt ccaagtattc agtttcacac aacagcaaac   360
actctgaatg cctttcctcc tgcccaacac aatg                               394

<210> SEQ ID NO 14
<211> LENGTH: 361
<212> TYPE: DNA
<213> ORGANISM: Homo sapiens
<220> FEATURE:
<221> NAME/KEY: unsure
<222> LOCATION: (7)
<223> OTHER INFORMATION: n=A,T,C or G
<220> FEATURE:
<221> NAME/KEY: unsure
<222> LOCATION: (249)
<223> OTHER INFORMATION: n=A,T,C or G
<220> FEATURE:
<221> NAME/KEY: unsure
<222> LOCATION: (258)
<223> OTHER INFORMATION: n=A,T,C or G

<400> SEQUENCE: 14
agcaggnact ataattttat aattaatttt acaattcatg tagcaaatgg aaaatcatac    60
agagaggcca atgtatataa ataagagttt atacagaaac tgccaattca caaaacagca   120
ctgcatggtt tctatattgc aagcacaaga catggtcaca tggttccact gtacaggtag   180
aaacaagccc acagacaata catagagtac cacctgaaac gaggcccttg gagctgctca   240
gcttcttana aaatagaaa ctttcaatgg tcataataca ttttgattca aaatgtcttc   300
taaaatgttt tcattgtggg agaaaattaa gaagggcaa aaatccatct atggaacttc    360
t                                                                   361

<210> SEQ ID NO 15
<211> LENGTH: 537
<212> TYPE: DNA
<213> ORGANISM: Homo sapiens
<220> FEATURE:
<221> NAME/KEY: unsure
<222> LOCATION: (460)
<223> OTHER INFORMATION: n=A,T,C or G

<400> SEQUENCE: 15
acttacaaaa ttaattttat tttgcaaaac tcaacaaata cacgttcaga tctggtttct    60
cttcaaaaca tgtgtttgtt ttttaacaa acatgcaagt taatttggca tgccaaacat   120 cttttctctct agctcgcctt ggaaaaattt ttttcataac acaaacaagg gtgcaaatat   180
tgtccaaacc tatttacatt tttaccctct agaattcat acattaatat ttattgggag   240
gaaagcaaaa ctgcaaaaca tagtctttgg cattcacatt tgcttcagca gtataattaa   300
aaccttatat ttgttttaaa gataacagt ttgaaggaaa tttaataaat cttgttttgg   360
ctctgcaaag gagccactat atcaaagcat ttaactggag ctgttgagtt cctgctggta   420
gaatattact tccagcctat ttattagctt gtcttccggn ggcccaatac atgcttttt   480 ccctctacac tgaatgaaag tacaaaaaga aaaccatttc ttttccccaa cacaatg      537
```

<210> SEQ ID NO 16
<211> LENGTH: 547
<212> TYPE: DNA
<213> ORGANISM: Homo sapiens
<220> FEATURE:
<221> NAME/KEY: unsure
<222> LOCATION: (9)
<223> OTHER INFORMATION: n=A,T,C or G
<220> FEATURE:
<221> NAME/KEY: unsure
<222> LOCATION: (467)
<223> OTHER INFORMATION: n=A,T,C or G

<400> SEQUENCE: 16

| | | | | | |
|---|---|---|---|---|---|
| gggtgtggng | atgtatttat | tcataatata | ttttcagaac | acattaataa | tggagaataa | 60 |
| cacttattca | tatactgaat | ataacttttc | ctggagcact | ctagagcttg | tttggagttg | 120 |
| gagaatactg | ccaggctttt | cctaatctct | ttggtctttg | gaagtgggca | gggtttctca | 180 |
| aaccaagtgt | cttccatggg | ccattggcaa | aggcttccct | tcatcagctt | ggaggggcag | 240 |
| aaagaccatg | gcttcagcac | ttccattttg | gaaagaagta | acaaaaaagt | gaattaatga | 300 |
| gcaatcggaa | agactcaaag | catttttgtac | tccacagttc | atttcttcac | acaaacgtcc | 360 |
| attactgcag | cgggcatgaa | aaccggcagg | gtgttaggct | catggcctga | agagaagtca | 420 |
| catcaccagc | cgatgttttc | atgcaaaagg | caatcgtgat | gattcanaac | ctggttctga | 480 |
| atttctccag | gtgtgctcgt | gagctgaagg | tcatgcccat | tctgtgcatc | ctgtgcccaa | 540 |
| cacaatg | | | | | | 547 |

<210> SEQ ID NO 17
<211> LENGTH: 342
<212> TYPE: DNA
<213> ORGANISM: Homo sapiens

<400> SEQUENCE: 17

| | | | | | |
|---|---|---|---|---|---|
| acattaagaa | gctcctcttc | tagcatgtcc | ttaagaagcc | tgtcttgcag | cactttcata | 60 |
| tcttctttca | tcaaacacat | ctcggatgta | aaaacagttt | cttcactatc | agtattacag | 120 |
| aagacacttt | tagccaatga | agttttcaaa | agaagaaagc | ctctgttgtt | cgcttttttg | 180 |
| atatgcactg | aacttctgaa | atatcttttc | ccaaaagtcc | acaaattcct | tttccaaatc | 240 |
| tttttaaagac | tgtgaatctt | tttcaaaatt | ctccagctcc | tctatgataa | tgaattggaa | 300 |
| tttatcaagt | tttttaatcc | tagagtcctg | actttggatg | at | | 342 |

<210> SEQ ID NO 18
<211> LENGTH: 279
<212> TYPE: DNA
<213> ORGANISM: Homo sapiens

<400> SEQUENCE: 18

| | | | | | |
|---|---|---|---|---|---|
| catcataagg | ttttattcat | atatatacag | ggtattaaga | attaagagga | tgctgggctc | 60 |
| tgttcttggc | ttggaagatt | ctatttaatt | gaaactctct | gttcagaaag | caataacttt | 120 |
| gtctcgttcc | tgttgggctg | aaccctaagg | tgagtgtgca | gtacagtgtg | tgtgggtgaa | 180 |
| atggagattt | ggaattgaac | tctctgcctg | taaatgttcc | ccaaataatt | gttgtgtgta | 240 |
| tgatacgtgt | ataataaaag | tattcttgtt | agaatctga | | | 279 |

<210> SEQ ID NO 19
<211> LENGTH: 239
<212> TYPE: DNA
<213> ORGANISM: Homo sapiens

<400> SEQUENCE: 19

```
ctgccagcgt ttttgtgtgg ctgcagtgtg cctgggccca gctcacgggc agtgggtgga     60
cctaactgcc caggcaggcg agagctactt ccagagcctt ccagtgcatg ggagggcagg    120
gctaggtgta gcggtgtctc ctctttgaaa ttaagaacta tctttcttgt agcaaagctg    180
cacctgatga tgctgcctct cctctctgtg ttgtctgggc ccttgtttac aagcacgcg     239
```

<210> SEQ ID NO 20
<211> LENGTH: 527
<212> TYPE: DNA
<213> ORGANISM: Homo sapiens

<400> SEQUENCE: 20

```
ctgaaccatt atgggataaa ctggtgcaaa ttctttgcct tctctacttc tcactgattg     60
aacataagct tccagggctc ccctgatgag gaggagcctg tccttttcag atggatggtc    120
atccagccac tgagagaagc gtgtgtggga ccactctgcc ctctggaaag gagatttcag    180
ttcagcgggt gctctcgtga acaaaaactg aataatgatg ctgaacggaa tcacatcccc    240
caatgcagga ctactggcta catgttcact tgcctggaag agcagaggtc tgaatgatct    300
cagcatccga taggactttc ctaaatcaga tactcgtcta cagaatgaac ccacagccaa    360
ctccatctgt gcaaaatcag cagcaagtcg cattttccca ccttcaccaa gaggtcttat    420
gagactggca tggcggataa aaagttcaac agctcttttgg gcaataaccct cagtgttgtc    480
aaagacaaaa tccaagcatt caaagtgttt aaaatagtca ctcataa                  527
```

<210> SEQ ID NO 21
<211> LENGTH: 399
<212> TYPE: DNA
<213> ORGANISM: Homo sapiens

<400> SEQUENCE: 21

```
ctgcaatggt tgcaagtgct atttccacct agctctgact ctccacttct aaccagacaa     60
acagccaacc aaccaatcaa catgtattta ataaccacct atggggtgca agcacaaaa    120
gggcactcat cttgaaaagg aaagaccaag aatgtgctag agtaaagaga cagagaccag    180
accctactct caagatcaag agacttcagt ctcggagaca tctgccattt ctctcttctt    240
aataaacctc atttgccttt aaaaatacat ttgctttggg ggcccagaat caagaaagga    300
aactttacaa agtaaacaga agttactccc cacagggagg cagaagcaga ttaaccccaa    360
cagcagacat ctgcccggaa gagcaaactc cacatctgg                           399
```

<210> SEQ ID NO 22
<211> LENGTH: 532
<212> TYPE: DNA
<213> ORGANISM: Homo sapiens

<400> SEQUENCE: 22

```
ccagaaggtg aagaaaagtt atctgataat gctcaaagtg cagtagaaat acttttaacc     60
attgatgata caaagagagc tggaatgaaa gagctaaaac gtcatcctct cttcagtgat    120
gtggactggg aaaatctgca gcatcagact atgcctttca tcccccagcc agatgatgaa    180
acagatacct cctatttga agccaggaat actgctcagc acctgaccgt atctggattt    240
agtctgtagc acaaaaattt cctttttagt ctagcctcgt gttatagaat gaacttgcat    300
aattatatac tccttaatac tagattgatc taaggggaaa agatcattat ttaacctagt    360
```

-continued

| tcaatgtgct tttaatgtac gttacagctt tcacagagtt aaaaggctga aaggaatata | 420 |
| gtcagtaatt tatcttaacc tcaaaactgt atataaatct tcaaagcttt tttcatctat | 480 |
| ttattttgtt tattgcactt tatgaaaact gaagcatcaa taaaattaga gg | 532 |

<210> SEQ ID NO 23
<211> LENGTH: 215
<212> TYPE: DNA
<213> ORGANISM: Homo sapiens

<400> SEQUENCE: 23

| tgcaaataag ggctgctgtt tcgacgacac cgttcgtggg gtccctggt gcttctatcc | 60 |
| taataccatc gacgtccctc cagaagagga gtgtgaattt tagacacttc tgcagggatc | 120 |
| tgcctgcatc ctgacacggt gccgtcccca gcacggtgat tagtcccaga gctcggctgc | 180 |
| cacctccacc ggacacctca gacacgcttc tgcag | 215 |

<210> SEQ ID NO 24
<211> LENGTH: 215
<212> TYPE: DNA
<213> ORGANISM: Homo sapiens

<400> SEQUENCE: 24

| cctgaggctc caggctaaga agtagccaag tttcacctgg agagaagagt agagggactt | 60 |
| cccaaatttc ttcctgaact cagctctgat actcagaagg tcagtctcac atcgagagat | 120 |
| aaggatgcga atcaggactt ggtaattggg ctcagtttcc tagtagggga agaaagagat | 180 |
| gggggggtagt tagtgagagt ctcactgaga gtagg | 215 |

<210> SEQ ID NO 25
<211> LENGTH: 530
<212> TYPE: DNA
<213> ORGANISM: Homo sapiens

<400> SEQUENCE: 25

| ttttttttct agtaagacta gatttattca ataccctagt aaaagttttg attataagta | 60 |
| tccaacagta taaaaagtac aaaacagatc tgtagatttc taatatatta atacaaagtg | 120 |
| catgactaca tacagtacat cctacaggca aagagaggtg gaaggggaaa aagaagactg | 180 |
| tggttgaggt ctagtaataa ataaataaat acagaagtag agatgatcca tattatagta | 240 |
| tattctacca ccaatactgc agccaaaatg tacaaaaaaa atcatttcaa ataactcagg | 300 |
| aggatgataa tggctggact tttgtaattc acctcaaaga ctgtgggaga gccaactcaa | 360 |
| ctcactgtat agtctgtgca tatggtggct tgtagcatgt aggttttttc caaagaagg | 420 |
| aaatataaaa tgtttagatt aagaactata aaactacagg gtgcctataa aaggtggctt | 480 |
| actccttatt gttattatac tatccaattt ttaaaatgca gtttaaaaaa | 530 |

<210> SEQ ID NO 26
<211> LENGTH: 366
<212> TYPE: DNA
<213> ORGANISM: Homo sapiens

<400> SEQUENCE: 26

| ccagcagttc tcggacctcc tctgggggca gggagaggcc attgggtcag ggctggacc | 60 |
| caggaggagt tggaatgggt gaaagatggg gagcaagttt ttagggtaca gggtgggcct | 120 |
| aagatgggtc agtagacaga tgggagcaca gagcagggca ggggtgagg tcaagtgagg | 180 |
| gccacaggat gtgctgaggg ctcccaggga gccctaccca ggctcacgtc ctcctggtca | 240 |

-continued

```
ccacctgtac tgtctggggt ccacaggtg tgggcgttgc cagggagcac tgggagggcc    300
tcggtagggt ccacctgtag ggagaggatg tcaggaccac tagcctctgg gcaagggcag    360
aggagg                                                               366

<210> SEQ ID NO 27
<211> LENGTH: 331
<212> TYPE: DNA
<213> ORGANISM: Homo sapiens
<220> FEATURE:
<221> NAME/KEY: unsure
<222> LOCATION: (241)
<223> OTHER INFORMATION: n=A,T,C or G

<400> SEQUENCE: 27
ccaaactcag agatggtacc agccaggggc aagcatgacc agagccaggg accctgtggc     60
tctgatcccc catttatcca ccccatgtgc ctcaggacta gagtgagcaa tcataccta    120 taaatgactt ttgtgccttt ctgctccagt ctcaaaattt cctacacctg ccagttcttt    180 acattttcc aaggaaagga aaacggaagc agggttcttg cctggtagct ccaggaccca    240
nctctgcagg cacccaaaga ccctctgtgt ccagcctctt ccttgagttc tcggaacctc    300
ctccctaatt ctcccttcct tccccacaag g                                  331

<210> SEQ ID NO 28
<211> LENGTH: 530
<212> TYPE: DNA
<213> ORGANISM: Homo sapiens

<400> SEQUENCE: 28
ccatgaatgc ccaacaagat aatattctat accagactgt tacaggattg aagaaagatt     60
tgtcaggagt tcagaaggtc cctgcactcc tagaaaatca agtggaggaa aggacttgtt    120
ctgattcaga agatattgga agctctgagt gctctgacac agattctgaa gagcagggag    180
accatgcccg ccccaagaaa cacaccacgg accctgacat tgataaaaaa gaaagaaaaa    240
agatggtcaa ggaagcccag agagagaaaa gaaaaaacaa aattcctaaa catgtgaaaa    300
aaagaaagga gaagacagcc aagacgaaaa aaggcaaata gaatgagaac catattatgt    360
acagtcattt tcctcagttc cttttctcgc ctgaactctt aagctgcatc tggaagatgg    420
cttattggtt ttaaccagat tgtcatcgtg gcactgtctg tgaagacgga ttcaaatgtt    480
ttcatgtaac tatgtaaaaa gctctaagct ctagagtcta gatccagtca                530

<210> SEQ ID NO 29
<211> LENGTH: 571
<212> TYPE: DNA
<213> ORGANISM: Homo sapiens
<220> FEATURE:
<221> NAME/KEY: unsure
<222> LOCATION: (412)
<223> OTHER INFORMATION: n=A,T,C or G

<400> SEQUENCE: 29
ccataatatt ctgatgatca aggagcacac atatacaaaa gttattggat tactgcaatt     60
ctcagaggca caaaacctga catggtgtga tatagtatat aatcagtcac ggggggggaaa    120 agaacattaa gtctttaaaa aggcttagga agacataaac agtaaatctt tgtttttcta    180
ccttcctttg gacagtgtta tatttcactt tcttctttgc aaaatgtttc caaattcatt    240
tgctcaggat ttatttaaga taataactta aaacaactaa cagttgttta tgctatatgc    300
```

-continued

| | |
|---|---|
| atatcatgca tgttctactg gttcaaggac aaaattaaaa caagatcttc tctgtaaagc | 360 |
| aaatatattt attatgcact ttcatataca cagggatttt ttgagtacca angggataaa | 420 |
| ataaaacttt tacaatgtga aattcaatgt acatttttgg ctatttacat acctcaaacc | 480 |
| aagggaaaaa taaaagaaa gcatttgttt gcaactacat ttgctgagaa gtgtaaatgg | 540 |
| aggacattaa gcaaaacaaa tatttgcata g | 571 |

<210> SEQ ID NO 30
<211> LENGTH: 917
<212> TYPE: DNA
<213> ORGANISM: Homo sapiens

<400> SEQUENCE: 30

| | |
|---|---|
| actgccagag agtatgattt gaaggagatg ggagcagatg taattcttgg ctggaatctc | 60 |
| tcatttcaaa atcacttcac ataatggtgt catcatttaa acacttaaca gtcagtgcaa | 120 |
| ctgccactgt aacatctagt tggacaaaac cacaaggagg gggaggagaa aatgccatca | 180 |
| ctattatgtt aacaaacatt taatttaaat ggttgctgca ctagtaaatt tctgcagaaa | 240 |
| acagttttac ccgccccctt tcacagttcc aaattaatca aggatgcttt tctataatct | 300 |
| gatgcttagc aaattagctc atgattcaaa ttttgccctc ttgaagcaca tacccttt | 360 |
| attttaaaag tccattatag agaatttgga atatataagg tatttgaatt gcagaacacc | 420 |
| cctctaattc tgttaatata gcaaagacaa aacagtatca tatacatcaa gatcatactt | 480 |
| ttaaagtaag tttaaaggtc tcaattgccc agatattaaa tttatatttt ccttctatta | 540 |
| aaaaatatta catttcaatt ttgtaatatt gtaacatatt ttaagatgac cagcaagacc | 600 |
| tagtcaattt gaaaataccc ttgcattcca tacacaagct ataccataag taataaccca | 660 |
| agtatatgat gtgtaaaagt tggtgaaggt cataatactg aattttttg caaatgtaaa | 720 |
| ctgctttcca gtaatcagc accattttt actagactac attttaatca cttccttagc | 780 |
| tgcttacaac ctctacttag gcataaataa aagaatctga aattggtata tttccccttc | 840 |
| ctgctgtgtt aaccaaaaat actatttgac ttaaagatca aagagtcttt ttcctgaagg | 900 |
| ttttttgtttt taaatgt | 917 |

<210> SEQ ID NO 31
<211> LENGTH: 367
<212> TYPE: DNA
<213> ORGANISM: Homo sapiens
<220> FEATURE:
<221> NAME/KEY: unsure
<222> LOCATION: (124)
<223> OTHER INFORMATION: n=A,T,C or G

<400> SEQUENCE: 31

| | |
|---|---|
| tcttttcttt ctgtatttcc caaattacag ggagctatgc ccttggtatt gcacacagta | 60 |
| cactgcaaaa gattcacaag gttagttgaa agtcattttt gccctggtga ttcaaagctc | 120 |
| aaanaatttt ctagcataaa gtcttattaa aaattttaat caaaatatta tttgagttta | 180 |
| agtttaataa aacaatacca ctatatatac tctcaacaac ttcattatat aatcagtcct | 240 |
| atgaggttgt acttgctttt catatcacac tgattaagga caaaaataat tttgatgtac | 300 |
| atgtaccata cactgatatg caatctacac actgatgcat ttacatacat acaaccccaa | 360 |
| cacaatg | 367 |

<210> SEQ ID NO 32
<211> LENGTH: 847

```
<212> TYPE: DNA
<213> ORGANISM: Homo sapiens

<400> SEQUENCE: 32
cattgtgttg ggctggcagg atagaagcag cggctcactt ggacttttc accagggaaa      60 tcagagacaa tgatggggct cttccccaga actacagggg ctctggccat cttcgtggta     120
agtcctggat tttcctaata atcacaaact tccctgcttc ctcccttgtt aaagaatatt     180
atatttgatt gcacaatctt tattataaat ctaaaagga gtgcagtgga atcaacact      240 ttgaaatgaa atcgtgaaga ttaccaattt ccttcttttg ttgtttttta tgttgtattt     300
tacatagaaa aataaaccag aaagaaatga gtttaaaaaa ccatttagaa ttttttttag     360
ttaatgaatt aagtaatctt aatcacaggt tatattttcc acaacatttt cactttcttt     420
aaagttatgc ttttactagt ttttctaacc cacaaacaag aacacaggag ccacttctat     480
tttccaagat tacatgtctc ttagcatata gctaagaact ctacacgcct gggcttgata     540
cctgacacgc ttttaaaagt aaaaaatcgc agaattaaaa tcaaagcagt gtttgactct     600
agagaagttg gaggattat taagtaagta tttatgttta gctattatgt gccaaaagaa      660
aatgtcagcc tttggggatg gggggaaaga catacaacat tttaaagcca ttttttttcag   720 aaaagtaata cttctgttga ttgagaaagt cgtacatagt attatctaaa agagaaacgg     780
aatgttacag actgttaaa acctggatgt tacagactaa cttactcctt aactgtgttc     840
ttatagc                                                               847

<210> SEQ ID NO 33
<211> LENGTH: 863
<212> TYPE: DNA
<213> ORGANISM: Homo sapiens
<220> FEATURE:
<221> NAME/KEY: unsure
<222> LOCATION: (321)
<223> OTHER INFORMATION: n=A,T,C or G
<220> FEATURE:
<221> NAME/KEY: unsure
<222> LOCATION: (563)
<223> OTHER INFORMATION: n=A,T,C or G
<220> FEATURE:
<221> NAME/KEY: unsure
<222> LOCATION: (601)
<223> OTHER INFORMATION: n=A,T,C or G
<220> FEATURE:
<221> NAME/KEY: unsure
<222> LOCATION: (858)
<223> OTHER INFORMATION: n=A,T,C or G

<400> SEQUENCE: 33
cattgtgttg ggcttttatt tgagtttatg aacagaaata gaaagtatgg tgcttgggtt      60 ttgcccttc ttactcctga aagttaaatc agaagacact gatttcattt tgtgaaattt     120
agctcagaga ctattgatct tttgtttcat taatatgaac aactattagt aaaaaatagc     180
tttaacagca tttctgctga tatctagtaa tctattcttt taatgtgaaa ataagataaa     240
atgtcctgga gctaattcta gcttaaattt gccagtattt ctgtatgtca ttaagttttt     300
ttcctctaag gttggtaata naattttgtt aatctttgca tacctgatgg catctatgtc     360
aatgctgatt gggtaattat aaattctgtg ctaatttaaa acttaatttg cctcttaagg    420
tgattgtcct ctgagtaatg attgtagtta aatgaagtat agcttgcaac tatactatca    480
catgggtcgt taagtaaaaa taaataaacc aaatttgtct gagacaggct aagatcaatc    540
ttctcatcaa accaattttt ctntaagagc aatttcactt tcagttttag ggtggacatt    600
```

-continued

```
nttgaatgcc tcaaattaaa cgttatctat ttaatcttcc tggaatagtc tgtgaccaaa       660
aaggagggtg tgatatattt aggtgtaaat atatcacata tatggtgtga tatatttggg       720
atttatatat tcagctcatt ctctgtgaag aagtcttcct gactaaaatt ggtttcaaga       780
taaactaatt tctgttagta tttctactct gcctaccatg tatgccttt tgttagaaac        840 taataaatgt atcagtcnct agc                                               863
```

<210> SEQ ID NO 34
<211> LENGTH: 432
<212> TYPE: DNA
<213> ORGANISM: Homo sapiens

<400> SEQUENCE: 34

```
agtgcatttc ctcttgattt gtctgggtta aaaccattcc ttttgtatga aatgttttga        60
cttaggaatc attttatgta cttgttctac ctggattgtc aacaactgaa agtacatatt       120
tcatccaaat caagctaaaa tgtatttaag ttgattctga gagtacaggt cagtaagcct       180
cattatttgg aatttgagag aaggtatagg tgatcggatc tgtttcattt ataaaaggtc       240 cagttttag gactagtaca ttcctgttat tttctgggtt ttatcatttt gcctaaaata        300
ggatataaaa gggacaaaaa ataagtagac tgtttttatg tgtgaattat atttctacta       360
aatgtttttg tatgactgtg ttatacttga taatatatat atatatatat atatatatca      420
acttgttaaa tt                                                          432
```

<210> SEQ ID NO 35
<211> LENGTH: 350
<212> TYPE: DNA
<213> ORGANISM: Homo sapiens

<400> SEQUENCE: 35

```
ccagagggt gtttatctta gggttggaat gtttctgatt atgctgacaa tagccattag         60
gctgatgttt tggggctgga tttaggcagt ttttaaataa aagagaactt aaaatggtgg       120
tgtttgtcca agatggtgat gttcctgctg tcaattagca taaacaaaag agaattctga       180
taccctgttg gaatgtcctc attcctctga gcttctccac tcacaggata aatgcaggag       240
tggcttcccc tcatggacac ctgcaaatgc agagtgtggg ggctctcctg gccctgcatc       300
actagcaaga gcaaaagctg ctccgagtct tgtttttaga acctggtcga                 350
```